US009099212B2

(12) United States Patent  
Thomas

(10) Patent No.: US 9,099,212 B2  
(45) Date of Patent: Aug. 4, 2015

(54) LOW VOLUMETRIC DENSITY BETAVOLTAIC POWER DEVICE

(75) Inventor: Chris Thomas, Ithaca, NY (US)

(73) Assignee: WIDETRONIX, INC., Ithaca, NY (US)

( * ) Notice: Subject to any disclaimer, the term of this patent is extended or adjusted under 35 U.S.C. 154(b) by 426 days.

(21) Appl. No.: 13/492,874

(22) Filed: Jun. 10, 2012

(65) Prior Publication Data

US 2013/0033149 A1     Feb. 7, 2013

Related U.S. Application Data

(60) Provisional application No. 61/515,938, filed on Aug. 7, 2011.

(51) Int. Cl.
*G21H 1/02*     (2006.01)
*G21H 1/06*     (2006.01)
*A61N 1/378*   (2006.01)

(52) U.S. Cl.
CPC .  *G21H 1/06* (2013.01); *A61N 1/378* (2013.01)

(58) Field of Classification Search
CPC .................................. G21H 1/00; G21H 1/02
USPC ...................... 310/303, 305; 257/428; 438/19
See application file for complete search history.

(56) References Cited

U.S. PATENT DOCUMENTS

| 2,819,414 | A | * | 1/1958 | Sherwood et al. ............ 310/303 |
| 4,024,420 | A | * | 5/1977 | Anthony et al. .............. 310/303 |
| 5,082,505 | A | * | 1/1992 | Cota et al. .................... 136/253 |
| 5,235,232 | A | * | 8/1993 | Conley et al. ................. 310/303 |
| 5,260,621 | A | * | 11/1993 | Little et al. .................... 310/303 |
| 6,118,204 | A | * | 9/2000 | Brown .......................... 310/303 |
| 6,238,812 | B1 | * | 5/2001 | Brown et al. ..................... 429/5 |
| 6,774,531 | B1 | * | 8/2004 | Gadeken ....................... 310/303 |
| 7,663,288 | B2 | * | 2/2010 | Chandrashekhar et al. .. 310/303 |

* cited by examiner

*Primary Examiner* — Burton Mullins
(74) *Attorney, Agent, or Firm* — Maxvalueip LLC

(57) ABSTRACT

One example is a betavoltaic cell that has been fabricated using a semiconductor that includes, but is not limited to, Silicon Carbide (SiC), Silicon (Si), Gallium Arsenide (GaAs), Indium Gallium Arsenide (InGaAs), Gallium Nitide (GaN), Gallium Phosphide (GaP), or Diamond, and uses through wafer via holes or other fabrication techniques to form both positive (+ve) and negative (−ve) contacts on the front and back sides of the cell. In another example, several of these cells with +ve and −ve contacts on the front and back sides of the cell are arranged vertically and/or horizontally to form customized parallel and/or series combinations that produce a close packed, energy dense betavoltaic composite unit, with increased power outputs relative to a single cell. In another example, tritium or a metal tritide is used as the radioisotope source for the cells.

8 Claims, 13 Drawing Sheets

Cross Section A-A

Batteries in Series:
- Voltage increases, current stays constant

Batteries in Parallel:
- Current increases, voltage stays constant

Batteries in Series and Parallel:
- Current and voltage increase

Cross Section A-A

Cross Section A-A

Batteries in Series:
- Voltage increases, current stays constant
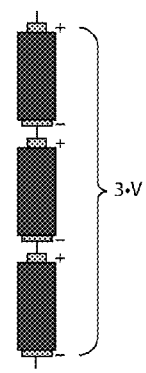
Figure 1(a)
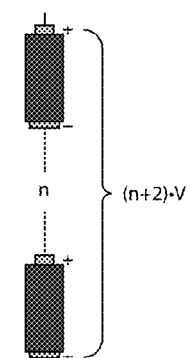
Figure 1(b)
Batteries in Parallel:
- Current increases, voltage stays constant
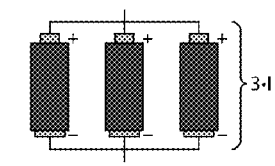
Figure 2(a)
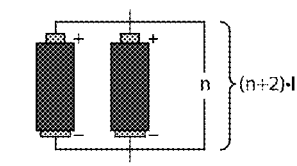
Figure 2(b)
Figure 9

Cross Section A-A

LOW VOLUMETRIC DENSITY BETAVOLTAIC POWER DEVICE

RELATED APPLICATIONS

This application is based on a prior provisional application, Ser. No. 61/515,938, with the same title, inventor, and assignee, filed on 7 Aug. 2011, claiming benefit as its priority date, whose teaching is incorporated herein, by reference.

This application is also related to "HIGH POWER DENSITY BETAVOLTAIC BATTERIES", which we filed on 6 Aug. 2010, as Ser. No. 12/851,555, and the disclosure of which is incorporated herein, by reference. Ser. No. 12/851, 555, in turn, is based on a U.S. provisional application Ser. No. 61/231,863, filed on 6 Aug. 2009, as its priority date.

INTRODUCTION

Betavoltaics are radioisotope batteries that harvest the energy from beta radiation sources and perform direct conversion of this energy to electrical power. The electrical power output of a betavoltaic battery is in the form of a value of current at a particular value of voltage. The range of the overall power output is typically from nano Watts (nW) to milli Watts (mW), depending on the radioisotope used as a source. The short circuit currents ($I_{sc}$) of betavoltaics depend on the amount and type of radioisotope used and is also dependent on the area of the device. The range of $I_{sc}$ is from nano Amperes (nA) to milli Amperes (mA). The open circuit voltages ($V_{oc}$) for betavoltaics range from tenths of a volt (for example 0.4 V for a Si betavoltaic) to over 2 volts for betavoltaics made from wider bandgap semiconductors, e.g. Silicon Carbide (SiC), Gallium Nitride (GaN), and Diamond.

Betavoltaics have been traditionally fabricated with two discrete elements: a semiconductor diode convertor, a cell, and a radioisotope source deposited on its own substrate; however, the betavoltaic can also be fabricated as a single unit cell that incorporates the isotope onto the active area of the cell. Both types of betavoltaic configurations can be connected in series and parallel, to increase the final output voltage and current, respectively. In addition, as the radioisotope sources of the betavoltaics have very high energy densities, betavoltaics, if designed correctly, can also have high energy densities. Cell stacking in series and parallel and final device packaging will be key to realizing this high energy density device (See the Appendices 1-3).

Betavoltaics can be used for a wide range of low power applications, where high temperature, small size, and/or long lifetimes are important. For applications such as power supplies for medical implants and power supplies for low power wireless sensors, the power requirements fall into the single digit nW to 100's of μW, well within the natural range of betavoltaics. These applications not only take advantage of the long lifetimes of the batteries, but, more importantly, their small size. Chemical batteries, while they can be scaled down to the sizes required for these applications, end up, for lack of fuel volume at this size, having very short lifetimes. The challenge for the design and production of a betavoltaic for these applications is to take the high energy density inherent in the radioisotope source and produce a high energy density betavoltaic device that will generate the requisite power at the requite size. This challenge is realized by first maximizing the energy density of an individual cell, then decreasing the cell thickness to the smallest size possible. Next, the thin, single unit betavoltaic cells need to be integrated into close packed series and parallel arrangements that can be further packaged to suit the applications.

In general, all batteries have a positive (+ve) and a negative (−ve) terminal. For any two batteries, a voltage output greater than the voltage output of each individual battery can be obtained by connecting the two batteries in series. Two batteries are connected in series when the positive terminal of one battery is connected to the negative terminal of the other. This series arrangement will give an output voltage that is equal to the sum of the voltages of each battery. Additionally, if 'N' batteries are all connected to each other in a similar series connection scheme, the output voltage will be equal to the sum of the voltages of all 'N' batteries. Note that the output current of a series arrangement is equal to the lowest battery current of the 'N' batteries (See the Appendices 1-3).

Similarly, for any two batteries, a current output greater than the current output of each individual battery can be obtained by connecting the two batteries in parallel. Two batteries are connected in parallel, when the positive and negative terminals of one battery are connected respectively to the positive and negative terminals of another. This parallel arrangement will give an output current that is equal to the sum of the currents of each battery. By a similar extension as in the series case, if 'N' batteries are all connected to each other in a parallel scheme, the output current will be equal to the sum of the currents of all 'N' batteries. Note that, for a parallel arrangement of batteries, the final voltage output is equal to the lowest battery voltage of the 'N' batteries. 'N' batteries can be connected in series/parallel to form modules, and these modules can then be connected together in parallel/series.

The challenge for the close packing of the betavoltaics is how to arrange the cells in a vertical and/or horizontal arrangement and end up with a series and/or parallel electrical connection. This invention provides a practical and concise method for the stacking of betavoltaics in series and parallel arrangements to achieve high energy density devices.

SUMMARY OF THE INVENTIONS

One embodiment of this invention is a betavoltaic cell that has been fabricated using a semiconductor that includes, but is not limited to, Silicon Carbide (SiC), Silicon (Si), Gallium Arsenide (GaAs), Indium Gallium Arsenide (InGaAs), Gallium Nitride (GaN), Gallium Phosphide (GaP), or Diamond, and uses through wafer via holes or other fabrication techniques to form both positive (+ve) and negative (−ve) contacts on the front and back sides of the cell. In another embodiment of the invention, several of these cells with +ve and −ve contacts on the front and back sides of the cell are arranged vertically and/or horizontally to form customized parallel and/or series combinations that produce a close packed, energy dense betavoltaic composite unit, with increased power outputs relative to a single cell (See the Appendices 1-3).

In another embodiment of the invention, tritium or a metal tritide is used as the radioisotope source for the cells. In other embodiments, beta emitting radioisotope sources such as nickel-63, phosphorus-33, sulfur-35, and promethium can be used. Other sources that can be used in still other embodiments are radioisotope sources that emit both beta and alpha particles, both beta particles and gamma radiation, and those radioisotope sources that emit all three radiation types—beta, alpha, and gamma. One other embodiment of the invention uses a radioisotope source on a substrate made from, but not limited to, copper, stainless steel, molybdenum, and nickel and that source mounted on its substrate is brought into contact with the active area of a semiconductor diode convertor to form a two discrete component betavoltaic cell. Another possible embodiment uses a semiconductor convertor with the radioisotope integrated/deposited onto the surface of the semiconductor diode convertor to form one single component betavoltaic cell. To illustrate and demonstrate the ideas of the invention, tritium or a metal tritide will be used as the radioisotope source, and SiC will be used as the semiconductor material, as examples.

BRIEF DESCRIPTION OF THE DRAWINGS

FIG. 9 shows schematic for a set of batteries in series and batteries in parallel.

DETAILED DESCRIPTION OF THE INVENTIONS

In one embodiment of the invention, a metal tritide is fabricated on the surface of a semiconductor diode convertor, to form a single unit betavoltaic cell. In another embodiment of the invention, the metal can be, but is not limited to, titanium, scandium, yttrium, hafnium, erbium, and zirconium, and the semiconductor used to fabricate the diode convertor can be, but is not limited to, SiC, GaN, GaAs, GaP, InGaAs, and diamond.

In a further embodiment of the invention, wafer through via hole technology or some other through or around wafer metal, or other conducting material, front to back connecting technology is used to create both positive (+ve) and/or negative (−ve) contacts on the front and/or back of the device cell. This new cell with front and/or backside positive and negative contacts can have at least three different configurations. In one embodiment, the top cell of the stack will have only a positive contact on the top and both negative and positive contacts on the bottom. In another embodiment of the invention, the bottom cell of the stack will have one negative contact on the backside and both a negative and positive contacts on the top side. The center cells will have positive and negative contacts on both the top and bottom of the cell, as shown in one embodiment.

Figure 1:
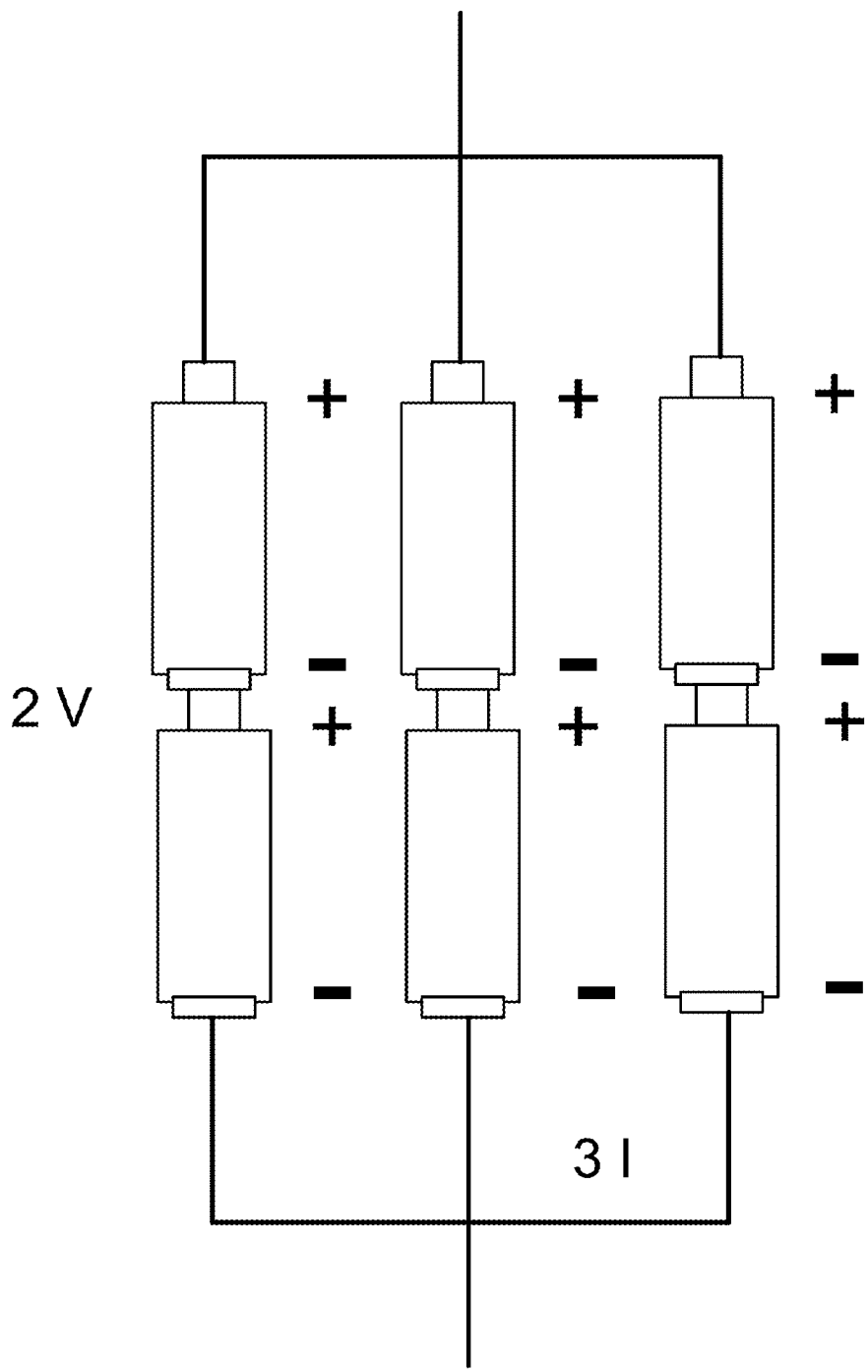
FIG. 1 shows batteries in series and parallel arrangement, to increase voltage and current, with twice the voltage and three times the current.
Figure 2:
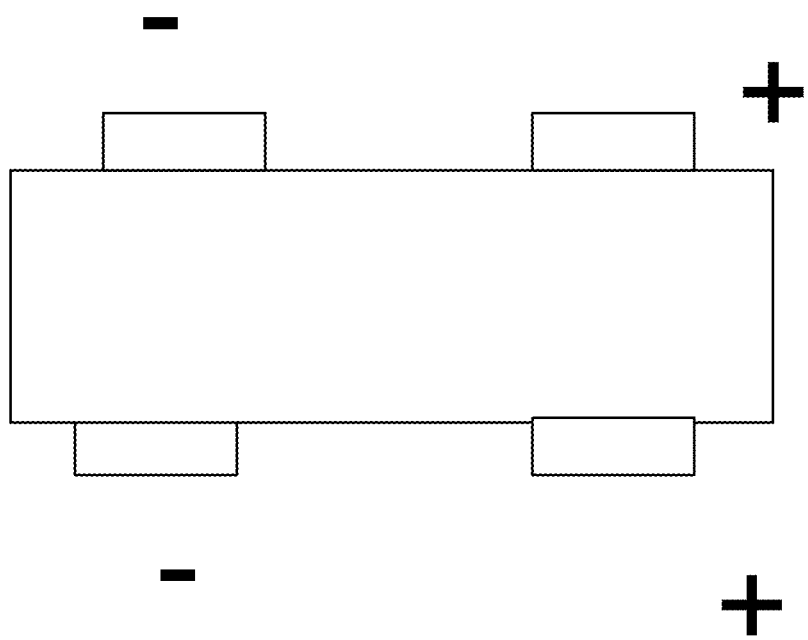
FIG. 2 shows schematic of Betavoltaic with top and bottom positive and negative contacts.

FIG. 1 shows batteries in series and parallel arrangement, to increase voltage and current, with twice the voltage and three times the current. FIG. 2 shows schematic of Betavoltaic with top and bottom positive and negative contacts.

In another embodiment of the invention, the front side positive and negative terminals of one cell are connected to the backside positive and negative terminals of another cell to produce a parallel arrangement of the two. Multiple cells can be connected together in this way to form 'N' devices in parallel. In yet another embodiment of the invention, the top side positive and negative terminals of one cell is connected respectively to the backside negative and positive terminals of another cell to produce a series arrangement of the two. Multiple cells can be connected together in this way, to form 'N' devices in series. Note that the connection between two cells with a positive and a negative contact on both front and back sides of the wafer is made into a series or parallel connection, just by rotating one cell relative to the other. In yet another embodiment of the invention, modules can be made that each have multiple cells connected in series/parallel, and then these modules of cells can be connected in parallel/series, to produce a final array unit that has the increased voltage determined by the series modules, and the increased current determined by the parallel modules. These betavoltaic array units can be used to customize the final output of the betavoltaic for any application.

Therefore, we are able to produce higher currents and higher voltages, using the combination of parallel and in-series stack of batteries, as described above. Thus, for still packed and small space, and long lifetime, we can get batteries for any desired voltages and currents, making it very flexible and useful for various applications, e.g. in medical, space, military, remote sensors, rough and unfriendly environments, locations which cannot be accessed easily, locations that humans cannot survive easily, locations that are very expensive to access routinely, weather forecasts, underwater exploration or sensing, or dangerous situations, e.g. too hot or too cold environments, or inside a spaceship, or inside a sensor at the edge of a cliff.

The connection between the single devices are done by evaporated metal, deposited metal, sputtering, plating, via holes, micro air bridge, wire bonding, or any other metal connections. The single devices can be rearranged, or alternatively, the metal mesh connections or rails or terminals or buses can be rotated or shifted, to cause serial or parallel connections or combinations between different or array of devices.

The radioactive material can be attached or close to the device(s), or it can be inserted or integrated into the semiconductor layers or between layers, for better efficiency or more compaction for packaging efficiency/smaller space/footprint. High Power Density Betavoltaic Batteries In the following section, we incorporate one of our related prior teachings, related to "HIGH POWER DENSITY BETAVOLTAIC BATTERIES", which we filed in a prior patent application, namely, Spencer7, or Ser. No. 12/851,555, filed 6 Aug. 2010, co-pending now, and the disclosure of which is incorporated herein, by reference. Ser. No. 12/851, 555, in turn, is based on a US provisional application Ser. No. 61/231,863, filed on 6 Aug. 2009, as its priority date.

Beta-voltaic devices have very high energy density and utilize radioisotopes as a fuel source. Radioisotope emissions originate from within a few microns of a radioactive material's surface at very low levels (nW/cm2–µW/cm2), despite the high power density in the bulk of the radioactive source (mW/cc–W/cc). Several semiconductor materials, such as Si, GaAs, GaP, GaN and diamond, may be used in betavoltaic devices.

However, silicon carbide (SiC) is the material used here for the production of beta voltaic devices, due to its wide bandgap. Moreover, in addition to its radiation hardness and ability not to degrade over time at higher temperatures and in harsh environments, SiC provides low leakage currents to effectively harvest low level emission rates from the isotope. The wide availability of high quality SiC substrates and epitaxy makes SiC the most practical of all semiconductors for beta-voltaics, when performance and efficiency are considered. For example, Si provides 100 times less power conversion efficiencies than SiC. Thus, betavoltaic devices made from Si are suboptimal, due to this poor efficiency.

Semiconductor-based beta-voltaic batteries find applications in several areas such as security systems and medical implants (e.g. pacemakers). In order to increase power in these and other applications in the presence of low emission levels from radioisotopes, it is necessary to take advantage of the energy density of the device and develop device geometries and packaging which maximize the size and utilization of radioisotope surface area. This invention uses novel device configurations and packaging to maximize power in betavoltaic batteries and power output per unit volume.

Beta-Voltaic Devices

A SiC based beta voltaic radioisotope battery can produce several nanowatts (nWs) to milliwatts (mWs) of power, at 1 to 2 volts, with theoretical efficiencies in excess of 30% and measured efficiencies of 20%. Radioisotopes provide fuel for these devices and emit high energy electrons, or beta particles. The radioisotope tritium may be used. Other radioactive materials, such as Nickel-63, Phosphorus-33 and Promethium, may also be used. Utilization of beta emitters is attractive because of the short penetration distance of emitted electrons. For example, a high energy electron emitted from nickel-63 is effectively stopped by 25 microns of plastic or a layer of dead skin. Moreover, beta particles do not damage semiconductor materials and are easily shielded from sensitive electronics.

For several decades, electronics have become smaller and ubiquitous. In addition, power requirements for silicon-based electronics have been made low enough to enable the realization of nanowatt electronics, and asynchronous logic platform technologies are either projecting or exhibiting a performance of 24pJ/instruction and 28 MIPS at 0.6V. Many medical applications can be powered with 1 to 10 microwatts (µWs) of average power. With such low power consumption requirements, a beta-voltaic battery source is able to continuously power the aforementioned electronics. Using these low power electronic elements, it is also possible to implement massive intelligent sensor networks which can monitor a large range of environments and infrastructures, or power a pacemaker or other implantable devices for over 25 years.

Silicon Carbide

SiC is a wide bandgap semiconductor, which is ideally suited for use in radioisotope batteries. The material's wide bandgap provides not only for radiation resistance in long term exposure to high energy electrons, but perhaps more importantly, the shunt resistance of SiC diodes is high enough to allow efficient extraction of energy from a radioisotope source. Silicon (Si), the semiconductor industry workhorse, cannot realize sufficiently high open circuit voltages or power conversion efficiencies to be an optimal alternative for beta-voltaic batteries. Recent improvements in SiC substrate and epitaxial technology will enable the low dislocation and defect densities required for realization of beta-voltaic devices (including batteries) which utilize this material.

Theory of a Radiation Battery

The operation of a radiation cell is well-described by the solar cell equations. The main relationship is given by $$V_{oc} = nV_T \ln(J_{gen}/J_{ss}) \quad (1)$$

where Voc is the open circuit voltage, n the ideality factor, $V_T$ the thermal voltage=25.9 mV at T=300K, $J_{gen}$ the current generated by the radioactive source, and $J_{ss}$ is the reverse saturation current of the diode used in the cell.

Using a tritium radiation source and SiC material, as illustrative examples, the current generated in the cell can be predicted as follows. The current generated in SiC by high energy electrons emitted from tritium is given as:

$$J_{gen} = (J_\beta * E_{mean\,\beta} * (1-\eta))/E_{e-h} \quad (2)$$

where $J_{Gen}$ is the net generated electron current, $J_\beta$ the net flux of beta electrons from the radiation source (~3 nA/cm² for tritiated water), $E_{mean\,\beta}$ the mean beta electron energy generated by tritium, which is 5.5 keV, $E_{e-h}$ the mean electron-hole pair creation energy, which is 5 eV for SiC, and $\eta$ which is the backscattering yield, which is (10%) for SiC.

It is worthwhile to mention that each high energy beta particle from tritium generates ~1100× (5.5 keV/5 eV) current in the cell due to this e-h pair creation energy. The expected maximum current density in SiC is ~2 µA/cm². This assumes 100% carrier collection efficiency in the absorption region. For SiC, this absorption region is ~0.5 µm. Such a predictive analysis can be carried out for any radiation source, such as Ni-63, Tritium, Phosphorus-33, Pm-147 or others (e.g. see the ref. MVS Chandrashekhar et al., Appl. Phys. Lett., 88, 033506 (2006)).

Radioisotopes

There are several candidate radioisotopes which can be inserted as a power source for beta-voltaic batteries. These radioisotopes include, but are not limited to Phosphorus-33, Ni-63, Promethium and Tritium. All of the sources share the following drawback. Although the Curie load is calculated from the total volume of the radioactive material, the amount of useable energy is limited to the number of high energy electrons which escape from the surface of the source before they can be reabsorbed. The self-absorption length of these radioisotopes is of the order of microns (ref. Everhart and Hoff, J. Appl. Phys, 42, 5837 (1971)). This means that the optimum thickness for the radioisotope source material (such as foil) is microns. Only electrons from a very thin layer of radioisotope source material are extracted. Therefore, to increase total power in a betavoltaic device, it is desirable to have greater radioisotope material and/or semiconductor surface area rather than greater radioisotope material volume.

Figure 3:
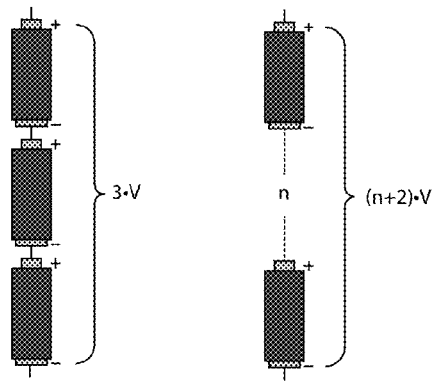
FIG. 3 shows schematic for a set of batteries in series, batteries in parallel, and batteries in series and parallel.
Figure 3:
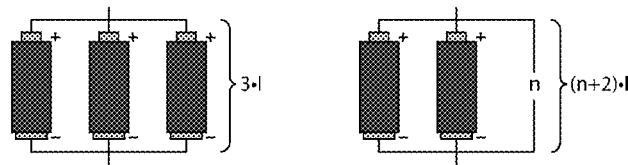
Figure 3:
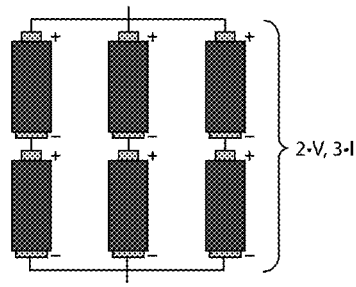
Figure 4:
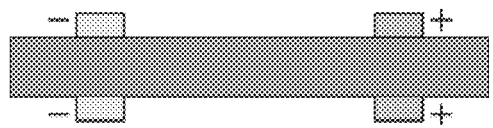
FIG. 4 shows schematic of Betavoltaic with top and bottom positive and negative contacts.
Figure 5:
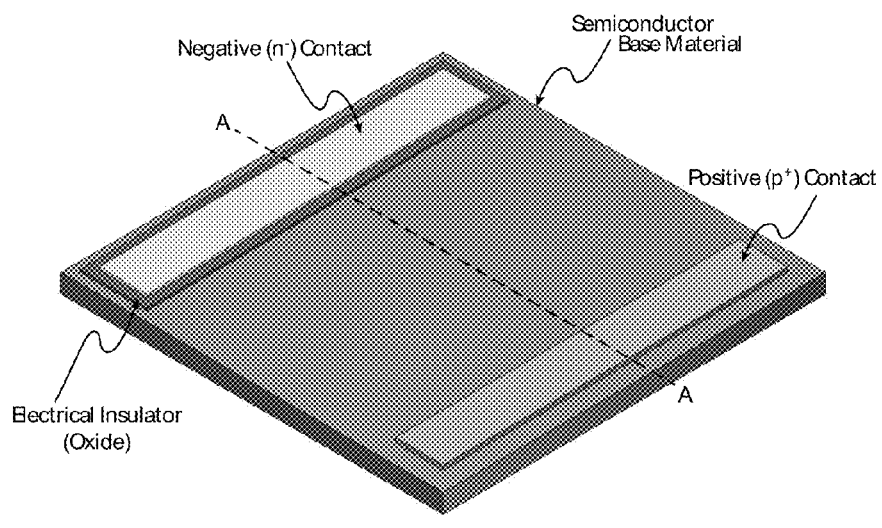
FIG. 5 shows schematic of Betavoltaic with top positive and negative contacts, with insulator in-between, from different point-of-views.
Figure 5:
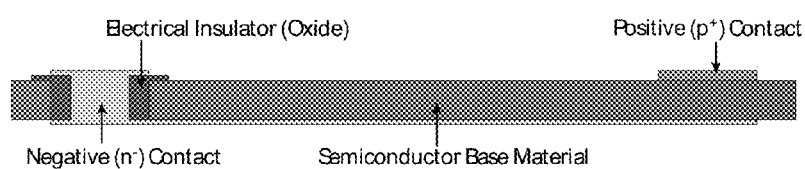
Figure 6:
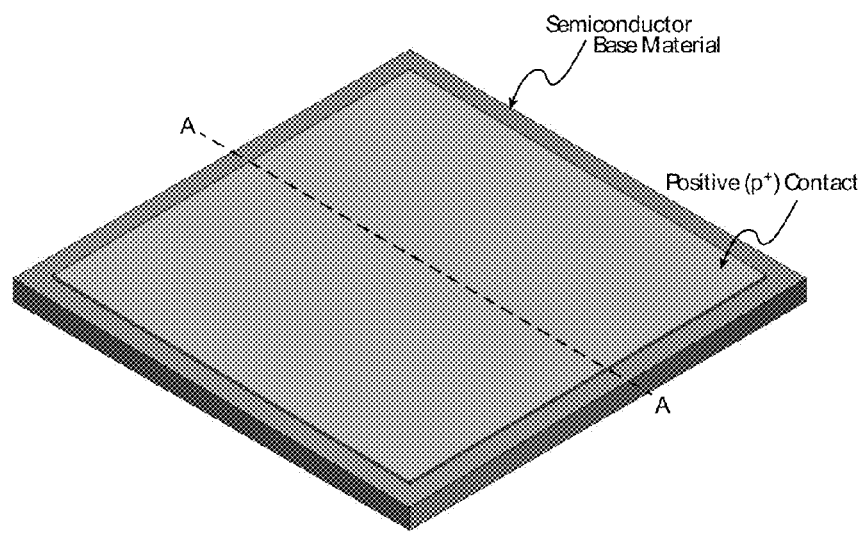
FIG. 6 shows schematic of Betavoltaic with top positive covering most of surface, and negative bottom contacts, with insulator in-between, from different point-of-views.
Figure 6:
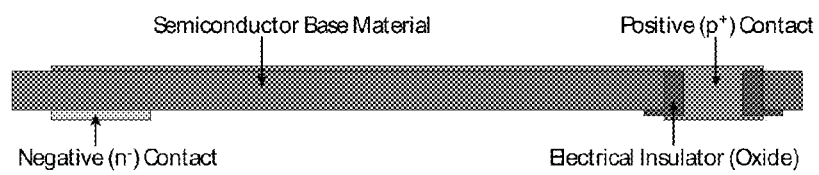

FIG. 3 shows schematic for a set of batteries in series, batteries in parallel, and batteries in series and parallel. FIG. 4 shows schematic of Betavoltaic with top and bottom positive and negative contacts. FIG. 5 shows schematic of Betavoltaic with top positive and negative contacts, with insulator in-between, from different point-of-views. FIG. 6 shows schematic of Betavoltaic with top positive covering most of surface, and negative bottom contacts, with insulator in-between, from different point-of-views.

Figure 7:
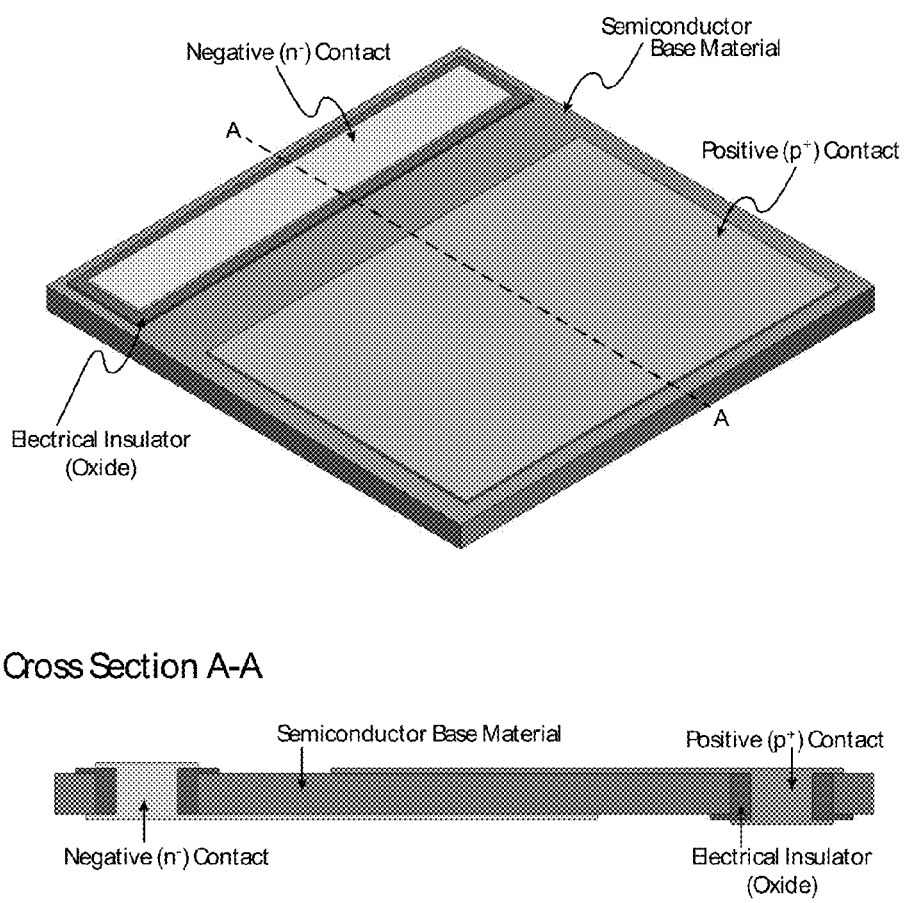
FIG. 7 shows schematic of Betavoltaic with top positive covering most of surface, and negative top contacts, with insulator in-between, from different point-of-views.
Figure 8:
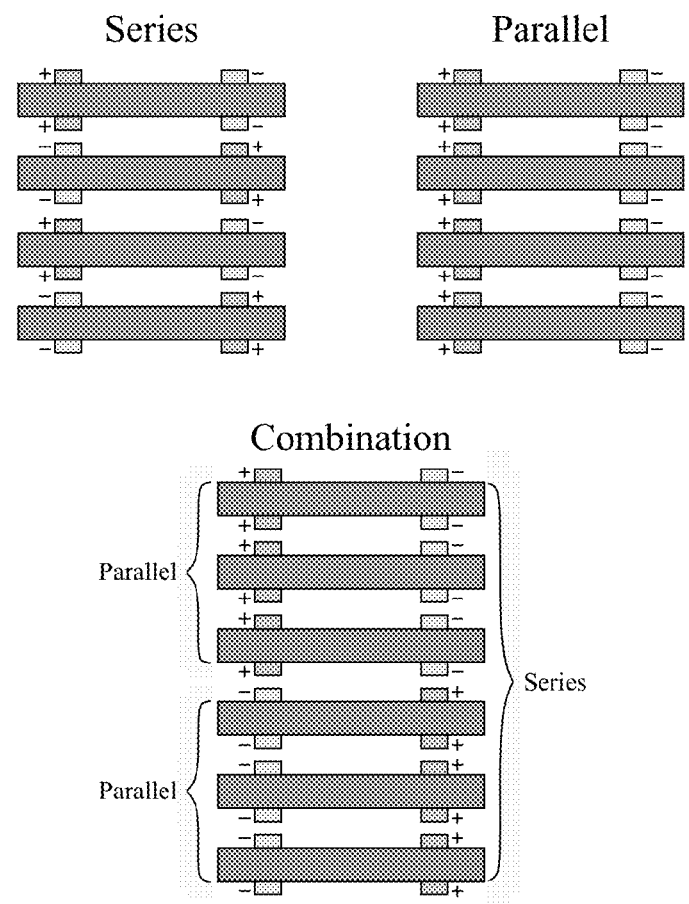
FIG. 8 shows schematic for a set of batteries in series, batteries in parallel, and batteries in series and parallel combination.
Figure 10:
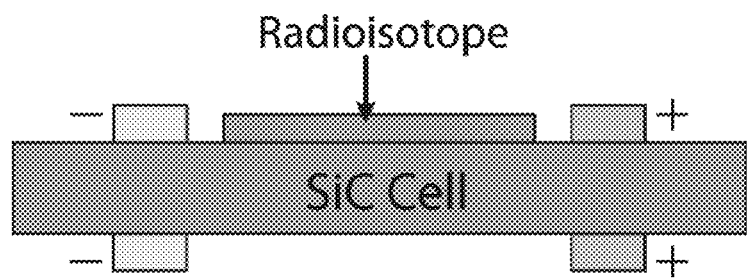
FIG. 10 shows schematic of Betavoltaic with top and bottom positive and negative contacts, with isotope on top surface in the middle, with SiC material.

FIG. 7 shows schematic of Betavoltaic with top positive covering most of surface, and negative top contacts, with insulator in-between, from different point-of-views. FIG. 8 shows schematic for a set of batteries in series, batteries in parallel, and batteries in series and parallel combination. FIG. 9 shows schematic for a set of batteries in series and batteries in parallel. FIG. 10 shows schematic of Betavoltaic with top and bottom positive and negative contacts, with isotope on top surface in the middle, with SiC material.

Figure 11:
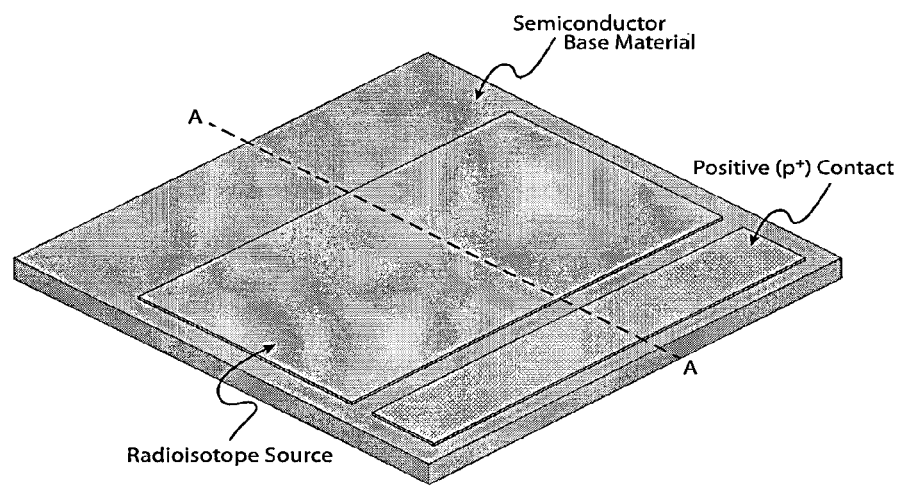
FIG. 11 shows schematic of Betavoltaic with top positive, with isotope source on top in the middle, and negative bottom contacts, with insulator in-between, from different point-of-views.
Figure 11:
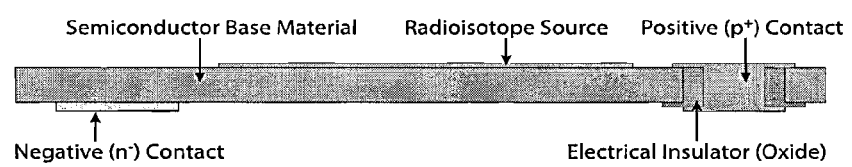
Figure 12:
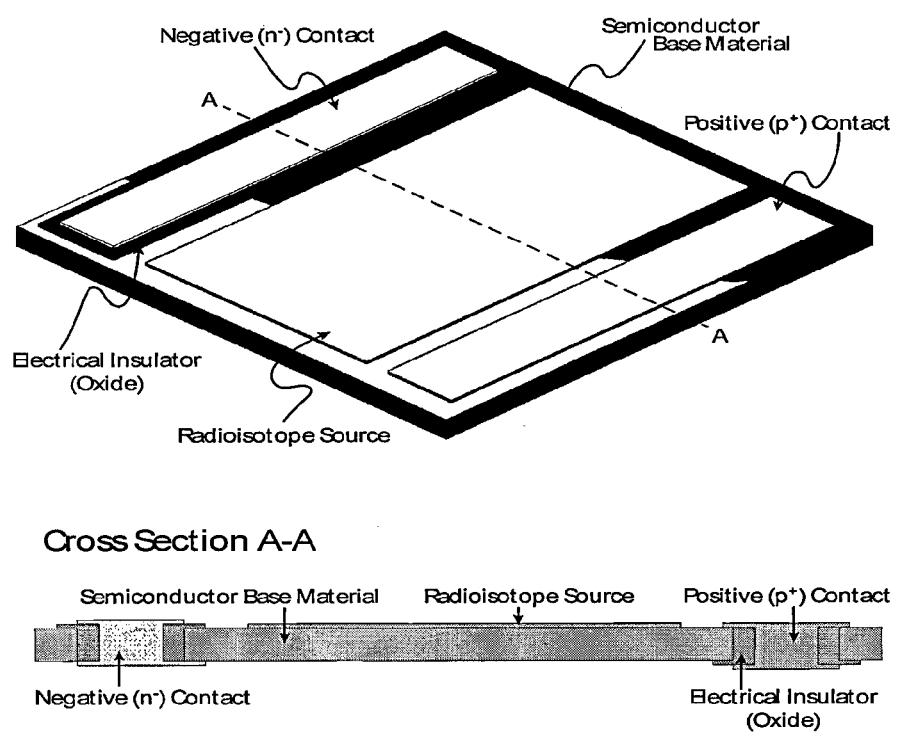
FIG. 12 shows schematic of Betavoltaic with top positive, with isotope source on top in the middle, and negative top contacts, with insulator in-between, from different point-of-views.
Figure 13:
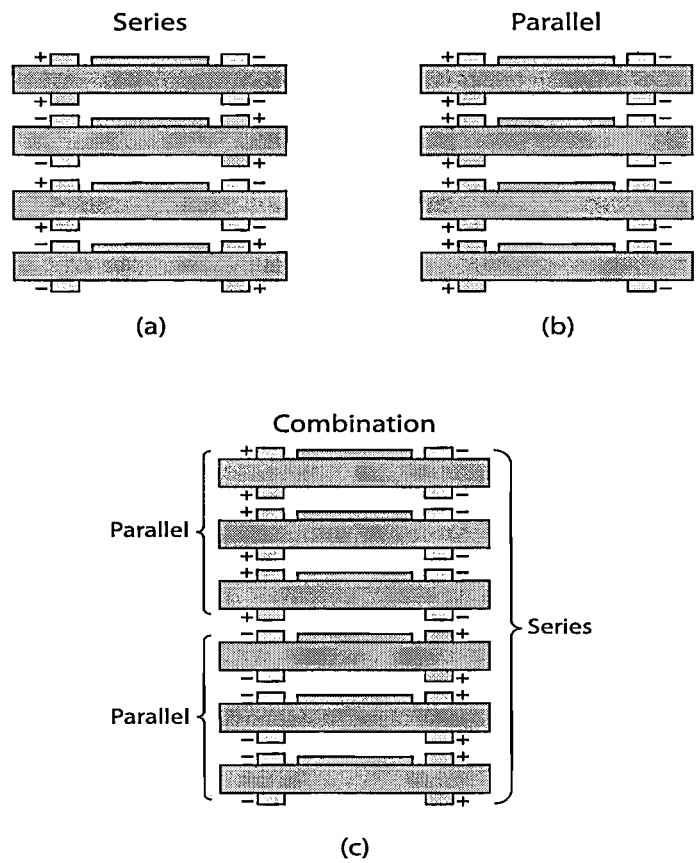
FIG. 13 shows schematic for a set of batteries in series, batteries in parallel, and batteries in series and parallel combination.

FIG. 11 shows schematic of Betavoltaic with top positive, with isotope source on top in the middle, and negative bottom contacts, with insulator in-between, from different point-of-views. FIG. 12 shows schematic of Betavoltaic with top positive, with isotope source on top in the middle, and negative top contacts, with insulator in-between, from different point-of-views. FIG. 13 shows schematic for a set of batteries in series, batteries in parallel, and batteries in series and parallel combination.

An embodiment of this invention is a high power density betavoltaic battery. In one embodiment of this invention, tritium is used as a fuel source. In other embodiments, radio-isotopes, such as Nickel-63, Phosphorus-33 or promethium, may be used. The semiconductor used in this invention may include, but is not limited to, Si, GaAs, GaP, GaN, diamond and SiC. For this disclosure, and for purposes of illustration/example only, tritium will be referenced as an exemplary fuel source, and SiC will be referenced as an exemplary semiconductor material.

Some of the Figures relate to Cross-Section and Perspective Views of Betavoltaic Device w/Elements and Case (Circular Geometry, Parallel Circuit Design); Cross-Section and Perspective Views of Betavoltaic Device w/Elements and Case (Square Geometry, Parallel Circuit Design); and Cross-Section and Perspective Views of Betavoltaic Device w/Elements and Case (Circular Geometry, Series and Parallel Circuit Design).

One embodiment of the invention is a circularly symmetric implementation. Square geometry may be employed, as well. Other geometries may be used to fit the application of interest.

The device is assembled one layer at a time, using various elements described below. This assembly may be performed manually or with robotic aid.

In one embodiment, the device is assembled in a case whose core is comprised of insulating material, such as aluminum oxide, and is plated with magnetic shielding material. Shielding materials, such as Fe, Ni, u (Mu)-Metal or any other material with a high magnetic susceptibility, may be used to screen stray and intentionally applied magnetic fields. The inside of the case is insulated to prevent device shorting.

In a further embodiment, the device is assembled in a case whose core is also comprised of insulating material such as aluminum oxide and is plated with electrical shielding material. Shielding materials such as Au, Ti, Fe, Ni, u (Mu)-Metal or any other material with a high electrical conductivity, may be used to screen stray and intentionally applied electrical fields. In a further embodiment, both electrical and magnetic shielding may be employed together. In a still further embodiment, a case can be made with two metal pieces fused together with an insulating material such as glass or aluminum oxide positioned between the metal pieces.

Cases for magnetic and/or electrical shielding comprise an isolation area in the center that is not plated with shielding material. The isolation area results in symmetric isolation between positively and negatively charged portions of the device.

Device with Parallel Circuit Design

Description of Device Elements for Parallel Circuit Design—Note: references to a "top side" indicates surfaces of a device which face toward the device cap, and references to a "bottom side" indicate surfaces of a device which face away from the device cap. Moreover, when comparing the position of elements with respect to other elements, "upper" indicates a position closer to the device cap, and "lower" indicates a position farther away from the device cap.

Element 1—

Split Ring Element. The element provides conduction feed-through for the package. In the drawings, region 1 or color red represents conduction regions, while region 2 or color white indicates insulating regions. This element is preferably fabricated from an insulating ceramic material, such as AlN, although other materials, such as SiO2 and sapphire, may be used. On top of this ceramic material, conduction material, such as thick gold plate, is deposited and electroplated, so as to form a low resistance path between the top and bottom of the element. A space is machined in the ceramic so as to accommodate the betavoltaic device (element 2 described below), which is inserted in the space.

Element 2—

SiC Betavoltaic Device. This element generates power. Yellow color or region 3 represents the device and green color or region 4 represents ohmic contacts used in the device. Ohmic contacts are deposited on both the top and bottom sides of the device, and the device is placed in a machined space inside of split ring element 1. In placing the betavoltaic device in the split ring element, an ohmic contact is made between the bottom side of the device and one side of isolation element 4 (described below), creating a positive polarity on that side of the overall device structure. Ohmic contact is also made between the top side of the betavoltaic device and one side of radioisotope element 3 (described below), creating a negative polarity on that side of the overall device structure. Contacts made by the betavoltaic device are electrically continuous on each side of the split ring assembly. The device (a PN junction semiconductor diode) has a P and N region. In the preferred implementation, the N-region is formed by chemical vapor deposition (CVD), while the p-region is formed by ion implantation and subsequent annealing.

Element 3—

Radioisotope Element. The element is a radioisotope foil (represented in grey or region 5) integrated with a conducting element, represented in red, or region 6. Insulating regions are represented in white, or region 7. In one implementation, the radioisotope is metal foil of titanium or scandium, which is irradiated by annealing in gaseous tritium. In other implementations/examples, tritium liquid may be used. Other radioisotopes mentioned herein may also be used in solid or fluid form. Insulating portions of the radioisotope element are fabricated from insulating material, such as AlN, although other materials, such as $SiO_2$ and sapphire, may be used. Conducting material shown in red, such as thick gold plate, is deposited and electroplated, so as to form a low resistance path between the top and bottom of the element.

Element 4—

Isolation Element. Conducting material is shown in red, and white regions indicate insulating areas. In one implementation, the isolation element is fabricated from insulating material, such as AlN, although other materials (such as $SiO_2$ and sapphire) may be used. Conducting material shown in red, such as thick gold plate, is deposited and electroplated, thus, forming a low resistance path between the top and bottom of the element.

In one embodiment of this invention, elements 1, 2, 3 and 4 (described above) are used to create a betavoltaic device which has a parallel circuit configuration. Each element is placed into a case.

The split ring element 1 is placed on top of the isolating element 4. SiC device element 2 is placed inside of split ring element 1 as described above. Radioisotope element 3 is placed on top of elements 1 and 2. A lid containing positive and negative terminals is placed on the entire element stack to complete the device.

The above set of elements may be configured in a single set or repeating sets, or stacks, which are configured in parallel, until the desired power output is achieved. For the invention described above, as an example, the total output power will be approximately 0.1 μW per cm$^2$ of SiC betavoltaic device area in a set/stack, multiplied by the number of sets/stacks. In other embodiments, higher and lower output power levels in each stack may be used. The assembly is closed with a press fit cap. This cap compresses the conductive areas and ensures a good quality contact between the layers. Although contact between elements is shown as direct contact, contact between elements may also be achieved with continuous solder or solder bumps, formed on conducting regions of each element.

Device with Series and Parallel Circuit Design

Description of Device Elements for Series and Parallel Circuit Design—Note: references to a "top side" indicate surfaces of a device which face toward the device cap, and references to a "bottom side" indicate surfaces of a device which face away from the device cap. Moreover, when comparing the position of elements with respect to other elements, "upper" indicates a position closer to the device cap, and "lower" indicates a position farther away from the device cap.

Element 1—

Split Ring Elements. The elements provide conduction feed-through for the package. In the drawings, red represents conduction regions, while white indicates insulating regions, with regions marked and labeled above. These elements are preferably fabricated from an insulating ceramic material, such as AlN, although other materials, such as SiO2 and sapphire, may be used. On top of this ceramic material, conduction material, such as thick gold plate, is deposited and electroplated, to form a low resistance path between the top and bottom of the element. A space is machined in the ceramic so as to accommodate the betavoltaic device (element 2 described below), which is inserted in the space.

Element 2—

SiC Betavoltaic Device: This element generates power. Yellow represents the device and green represents ohmic contacts used in the device. Ohmic contacts are deposited on both the top and bottom sides of the device and the device is placed in a machined space inside of split ring element 1. In placing the betavoltaic device in the split ring element, ohmic contact can be made with certain elements, based on the desired series configuration and the quantity of betavoltaic device elements utilized. Examples include:

a). qty. (quantity) two device elements 2 in series—the upper device element 2 makes ohmic contact between the top side of the device and one side of radioisotope element 3 (described below), creating a negative polarity on that side of the overall device structure. This same device also makes ohmic contact between the bottom side of the device and the top side of series element 5 (described below). The lower device element 2 makes ohmic contact between the top side of the device and bottom side of element 5. This same device element 2 makes ohmic contact between the bottom side of the device and one side of isolation element 4 (described below), creating a positive polarity on that side of the overall device structure.

b). qty. of more than two device elements in series—the configuration in a). above is used to start the series configuration, and the combination of element 5 and lower device element 2 mentioned in a) above is repeated and added to the lowermost portion of the series configuration, until the desired quantity of device elements configured in series is reached. The final lowermost device element 2 makes ohmic contact between the bottom side of the device and one side of isolation element 4 (described below), creating a positive charge on that side of the overall device structure.

The device element (a PN junction semiconductor diode) has a P and N region. In one implementation, the N-region is formed by chemical vapor deposition (CVD), while the p-region is formed by ion implantation and subsequent annealing, as discussed in relevant published literature.

Element 3—

Radioisotope Element: The element is a radioisotope foil (represented in grey) integrated with a conducting element, represented in red, as shown above for different regions. Insulating regions are represented in white. In one implementation, the radioisotope is metal foil of titanium or scandium, which is irradiated by annealing in gaseous tritium. In other implementations, tritium liquid may be used. Other radioisotopes mentioned herein may also be used in solid or fluid form. Insulating portions of the radioisotope element are fabricated from insulating material, such as AlN, although other materials, such as SiO$_2$ and sapphire, may be used. Conducting material shown in red, such as thick gold plate, is deposited and electroplated, so as to form a low resistance path between the top and bottom of the element.

Element 4—

Isolation Element: Conducting material is shown in red, and white regions indicate insulating areas. In one implementation, the isolation element is fabricated from insulating material such as AlN, although other materials such as SiO$_2$ and sapphire may be used. Conducting material shown in red, such as thick gold plate, is deposited and electroplated thus forming a low resistance path between the top and bottom of the element.

Element 5—

Series Element: This element contains a radioisotope foil (represented in grey). The element also contains isolation material (white regions) and conductive regions, indicated in red. In one implementation, the isolation element is fabricated from insulating material such as AlN, although other materials such as SiO$_2$ and sapphire may be used. Conducting material shown in red, such as thick gold plate, is deposited and electroplated on the outermost edge of the element, thus, forming a low resistance path between the top and bottom of the element at that outer edge. Conducting material which is proximal to the radioisotope foil is not plated, but instead is formed through the entire thickness of the element as a solid conductive ring, which also provides a low resistance path between the top and bottom of the element.

In one embodiment of this invention, elements 1, 2, 3, 4 and 5 (described above) are used to create a betavoltaic device which has series and parallel circuit configurations. Each element is placed into a case.

Split ring elements 1 containing device elements 2 are placed in series, in accordance with the above, and with series element 5 placed between each element 1 and 2 combination, also in accordance with the above. The desired quantity of device elements 2 (along with split ring and series element(s) 1 and 5, respectively) are placed on top of isolating element 4. Radioisotope element 3 is placed on top of uppermost device element 2. This configuration comprises one complete set of elements. A lid containing positive and negative terminals is placed on the entire configuration to complete the device.

The above set of elements may be configured in a single set or repeating sets, or stacks, which are configured in parallel, until the desired power output is achieved. For the invention described above, the total output power will be approximately 0.1 μW per cm$^2$ of SiC betavoltaic device area in a set/stack multiplied by the number of sets/stacks. In other embodiments, higher and lower output power levels in each set/stack may be used. The assembly is closed with a press fit cap. This cap compresses the conductive areas and ensures a good quality contact between the layers. Although contact between elements is shown as direct contact, contact between elements may also be achieved with continuous solder or solder bumps formed on conducting regions of each element.

We have the following features or parts: item 101 (Lid to Battery Case), 102 (negative post), 103 (positive post), 104 (case isolation material, or isolation material), 105 (radioisotope element, 106 (radioisotope), 107 (isolation material), 108 (metal contact), 109 (split ring element), 110 (SiC Betavoltaic device), 111 (ohmic contact), 112 (isolation material), 113 (metal contact), 118 (isolation element), 119 (isolation material), 120 (metal contact), 121 (battery case), and 122 (assembled device).

We have the following features or parts: item 201 (Lid to Battery Case), 202 (negative post), 203 (positive post), 204 (case isolation material, or isolation material), 205 (radioisotope element, 206 (radioisotope), 207 (isolation material), 208 (metal contact), 209 (split ring element), 210 (SiC Betavoltaic device), 211 (ohmic contact), 212 (isolation material), 213 (metal contact), 214 (isolation element), 215 (isolation material), 216 (metal contact), 217 (battery case), and 218 (assembled device).

We have the following features or parts: item 101 (Lid to Battery Case), 102 (negative post), 103 (positive post), 104 (case isolation material, or isolation material), 105 (radioisotope element, 106 (radioisotope), 107 (isolation material), 108 (metal contact), 109 (split ring element), 110 (SiC Betavoltaic device), 111 (ohmic contact), 112 (isolation material), 113 (metal contact), 114 (series element, or element), 115 (radioisotope), 116 (isolation material), 117 (metal contact), 118 (isolation element), 119 (isolation material), 120 (metal contact), 121 (battery case), and 301 (assembled device).

The devices can be grown on different materials or substrates, or implanted/annealed, or by any other deposition methods. They can be stacked on top of each other in series or side-by-side in parallel. The contacts may be by pressure, or no-pressure, surface adhesion, or by removal of the layer and its placement on a second substrate, or by flip-chip-type technology, reversing the orientation or direction.

The supplied material may be in shape of liquid, fluid, gas, powder, conventional semiconductor, polycrystalline, crystalline, amorphous, or combination of different crystalline regions.

The thickness of the active region can be non-uniform, or ramped thickness, variable thickness, so that different absorption or current is obtained.

The regions on the surface can be patterned so that for heat dissipation and transfer is done more efficiently, to reduce overheating, or increasing efficiency, if that effect is desired, to some optimum temperature.

The battery can be integrated on the same substrate, on same circuit, to save energy, cost, space, efficiency, or time, and increase speed.

Any other variations of the above are also meant to be included in the coverage or scope of this invention.

The invention claimed is:

1. A betavoltaic cell semiconductor device, said betavoltaic cell semiconductor device comprising:
   a substrate;
   a positive metal contact;
   wherein said positive metal contact goes through said substrate, from front of said substrate to back of said substrate;
   said positive metal contact is located near a first side of said substrate, along said first side of said substrate;
   a negative metal contact;
   wherein said negative metal contact goes through said substrate, from said front of said substrate to said back of said substrate;
   said negative metal contact is located near a second side of said substrate, along said second side of said substrate;
   said first side of said substrate is located opposite to said second side of said substrate;
   a first electrical insulator jacket;
   said first electrical insulator jacket goes through said substrate, from said front of said substrate to said back of said substrate;
   said first electrical insulator jacket covers said positive metal contact and isolates said positive metal contact from said substrate in all directions except for said front of said substrate;
   a second electrical insulator jacket;
   said second electrical insulator jacket goes through said substrate, from said front of said substrate to said back of said substrate;
   said second electrical insulator jacket covers said negative metal contact and isolates said negative metal contact from said substrate in all directions except for said back of said substrate;
   wherein said substrate is made of semiconductor material;
   a radioisotope source layer;
   said radioisotope source layer is located on top of said substrate, on said front of said substrate;
   said radioisotope source layer is located between said first electrical insulator jacket and said second electrical insulator jacket, in middle of said substrate;
   wherein said negative metal contact is connected to a second negative metal contact of a second device;
   wherein said positive metal contact is connected to a second positive metal contact of said second device.

2. The betavoltaic cell semiconductor device as recited in claim 1, wherein said betavoltaic cell semiconductor device comprises one or more of following materials: Silicon Carbide, Silicon, Gallium Arsenide, Indium Gallium Arsenide, Gallium Nitide, Gallium Phosphide, or diamond.

3. The betavoltaic cell semiconductor device as recited in claim 1, wherein said betavoltaic cell semiconductor device comprises one or more of following materials: tritium or a metal tritide.

4. The betavoltaic cell semiconductor device as recited in claim 1, wherein said betavoltaic cell semiconductor device comprises one or more of following materials: beta emitting radioisotope sources, nickel-63, phosphorus-33, sulfur-35, or promethium.

5. The betavoltaic cell semiconductor device as recited in claim 1, wherein said betavoltaic cell semiconductor device comprises one or more of following materials: copper, stainless steel, molybdenum, or nickel.

6. The betavoltaic cell semiconductor device as recited in claim 1, wherein said betavoltaic cell semiconductor device comprises a semiconductor diode convertor.

7. The betavoltaic cell semiconductor device as recited in claim 1, wherein said betavoltaic cell semiconductor device comprises an active area of a semiconductor diode convertor.

8. The betavoltaic cell semiconductor device as recited in claim 1, wherein said betavoltaic cell semiconductor device comprises one or more SiC betavoltaic cell units.

* * * * *